(12) United States Patent
Yeh

(10) Patent No.: US 9,114,244 B2
(45) Date of Patent: Aug. 25, 2015

(54) NEEDLELESS VALVE SYSTEM FLUID CONTROL

(75) Inventor: Jonathan Yeh, Diamond Bar, CA (US)

(73) Assignee: CareFusion 303, Inc., San Diego, CA (US)

( * ) Notice: Subject to any disclaimer, the term of this patent is extended or adjusted under 35 U.S.C. 154(b) by 267 days.

(21) Appl. No.: 13/360,180

(22) Filed: Jan. 27, 2012

(65) Prior Publication Data

US 2013/0197453 A1    Aug. 1, 2013

(51) Int. Cl.
*A61M 39/24* (2006.01)
*A61M 39/26* (2006.01)

(52) U.S. Cl.
CPC ....... *A61M 39/24* (2013.01); *A61M 2039/2433* (2013.01); *A61M 2039/263* (2013.01)

(58) Field of Classification Search
CPC .............. A61M 39/26; A61M 39/165; A61M 2039/267; A61M 39/24; A61M 39/22; A61M 2039/2433; A61M 2039/224; A61M 39/10; A61M 2039/266; A61M 2039/1033; A61M 2039/268; A61M 2039/1072; A61M 2039/0633
USPC ................................. 604/246, 247, 249, 256
See application file for complete search history.

(56) References Cited

U.S. PATENT DOCUMENTS

| 5,549,566 | A | 8/1996 | Elias et al. |
|---|---|---|---|
| 6,050,978 | A | 4/2000 | Orr et al. |
| 6,063,062 | A * | 5/2000 | Paradis .......................... 604/249 |
| 6,585,229 | B2 | 7/2003 | Cote et al. |
| 7,118,560 | B2 | 10/2006 | Bonaldo |
| 7,753,338 | B2 | 7/2010 | Desecki |
| 7,993,328 | B2 * | 8/2011 | Whitley ........................ 604/537 |
| 2002/0032433 | A1 * | 3/2002 | Lopez ............................ 604/533 |
| 2005/0121638 | A1 | 6/2005 | Doyle |
| 2007/0007478 | A1 | 1/2007 | Leinsing et al. |
| 2011/0028914 | A1 | 2/2011 | Mansour et al. |

OTHER PUBLICATIONS

International Search Report and Written Opinion for PCT/US2013/022587 mailed May 3, 2013.
International Preliminary Report on Patentability in PCT Application No. PCT/US2013/022587 dated Jul. 29, 2014.

* cited by examiner

*Primary Examiner* — Nicholas Lucchesi
*Assistant Examiner* — Weng Lee
(74) *Attorney, Agent, or Firm* — McDermott Will & Emery LLP

(57) ABSTRACT

A needleless valve system includes a cannula comprising a cannula tip; a valve comprising a valve tip, wherein the valve is disposed around the cannula; and a housing comprising a housing tip, wherein the cannula tip, the valve tip, and the housing tip comprise a flat surface when the needleless valve system is in a sealed position.

18 Claims, 6 Drawing Sheets

300

```
┌─────────────────────────────────────────────────────────────┐
│ SEAL A PORT OF A CANNULA BY A VALVE, WHEREIN THE PORT IS    │
│ DISPOSED ALONG A RADIUS OF THE CANNULA                      │
│ 310                                                         │
│  ┌────────────────────────────────────────────────────────┐ │
│  │ SEAL THE PORT BY A PROTRUSION DISPOSED IN THE PORT     │ │
│  │ 312                                                    │ │
│  └────────────────────────────────────────────────────────┘ │
└─────────────────────────────────────────────────────────────┘
                            │
                            ▼
┌─────────────────────────────────────────────────────────────┐
│ DEPRESS THE VALVE SUCH THAT THE VALVE UNCOVERS THE PORT     │
│ 320                                                         │
│  ┌────────────────────────────────────────────────────────┐ │
│  │ DEPRESS THE VALVE BY A NEEDLELESS DEVICE               │ │
│  │ 322                                                    │ │
│  └────────────────────────────────────────────────────────┘ │
└─────────────────────────────────────────────────────────────┘
                            │
                            ▼
┌─────────────────────────────────────────────────────────────┐
│ ALLOWING FLUID TO FLOW THROUGH THE PORT AND WITHIN THE      │
│ CANNULA                                                     │
│ 330                                                         │
└─────────────────────────────────────────────────────────────┘

┌─────────────────────────────────────────────────────────────┐
│ PREVENT RADIAL DEFORMATION OF THE VALVE AT THE PORT FROM    │
│ BACK PRESSURE IN THE CANNULA                                │
│ 340                                                         │
└─────────────────────────────────────────────────────────────┘

┌─────────────────────────────────────────────────────────────┐
│ SEAL A PORT OF A HOUSING BY THE VALVE                       │
│ 350                                                         │
└─────────────────────────────────────────────────────────────┘

┌─────────────────────────────────────────────────────────────┐
│ PROVIDE A FLAT SURFACE AT A PORT OF A HOUSING, WHEREIN THE  │
│ CANNULA AND THE VALVE ARE CO-PLANAR AT THE PORT OF THE      │
│ HOUSING                                                     │
│ 360                                                         │
└─────────────────────────────────────────────────────────────┘

┌─────────────────────────────────────────────────────────────┐
│ WIPING FLUID OFF OF AN OUTER SURFACE OF THE CANNULA BY      │
│ THE VALVE                                                   │
│ 370                                                         │
└─────────────────────────────────────────────────────────────┘
```

FIG. 3

NEEDLELESS VALVE SYSTEM FLUID CONTROL

BACKGROUND

Oftentimes, needleless valves include a large interior volume that results in a large amount of residual fluid within the needleless valve after use of the needleless valve. Among other things, the large amount of residual fluid, which was intended to be administered to a patient, is not actually administered to the patient.

Moreover, some needleless valves include a "straight through" fluid flow channel to reduce the amount of residual fluid within the needleless valve. In particular, such devices utilize a split-septum valve to control fluid flow in the "straight through" fluid flow channel. However, a split-septum valve can retain medical fluid, such as blood, which is difficult to remove from within the slit-septum. As a result, the retained blood within the split-septum can lead to the promotion of blood-borne diseases.

BRIEF DESCRIPTION OF THE DRAWINGS

FIG. 3 illustrates an embodiment of a method for controlling fluid flow in a needleless valve system.

The drawings referred to in this description should be understood as not being drawn to scale except if specifically noted.

DESCRIPTION OF EMBODIMENTS

Reference will now be made in detail to embodiments of the present technology, examples of which are illustrated in the accompanying drawings. While the technology will be described in conjunction with various embodiment(s), it will be understood that they are not intended to limit the present technology to these embodiments. On the contrary, the present technology is intended to cover alternatives, modifications and equivalents, which may be included within the spirit and scope of the various embodiments as defined by the appended claims.

Furthermore, in the following description of embodiments, numerous specific details are set forth in order to provide a thorough understanding of the present technology. However, the present technology may be practiced without these specific details. In other instances, well known methods, procedures, components, and circuits have not been described in detail as not to unnecessarily obscure aspects of the present embodiments.

Figure 1A:
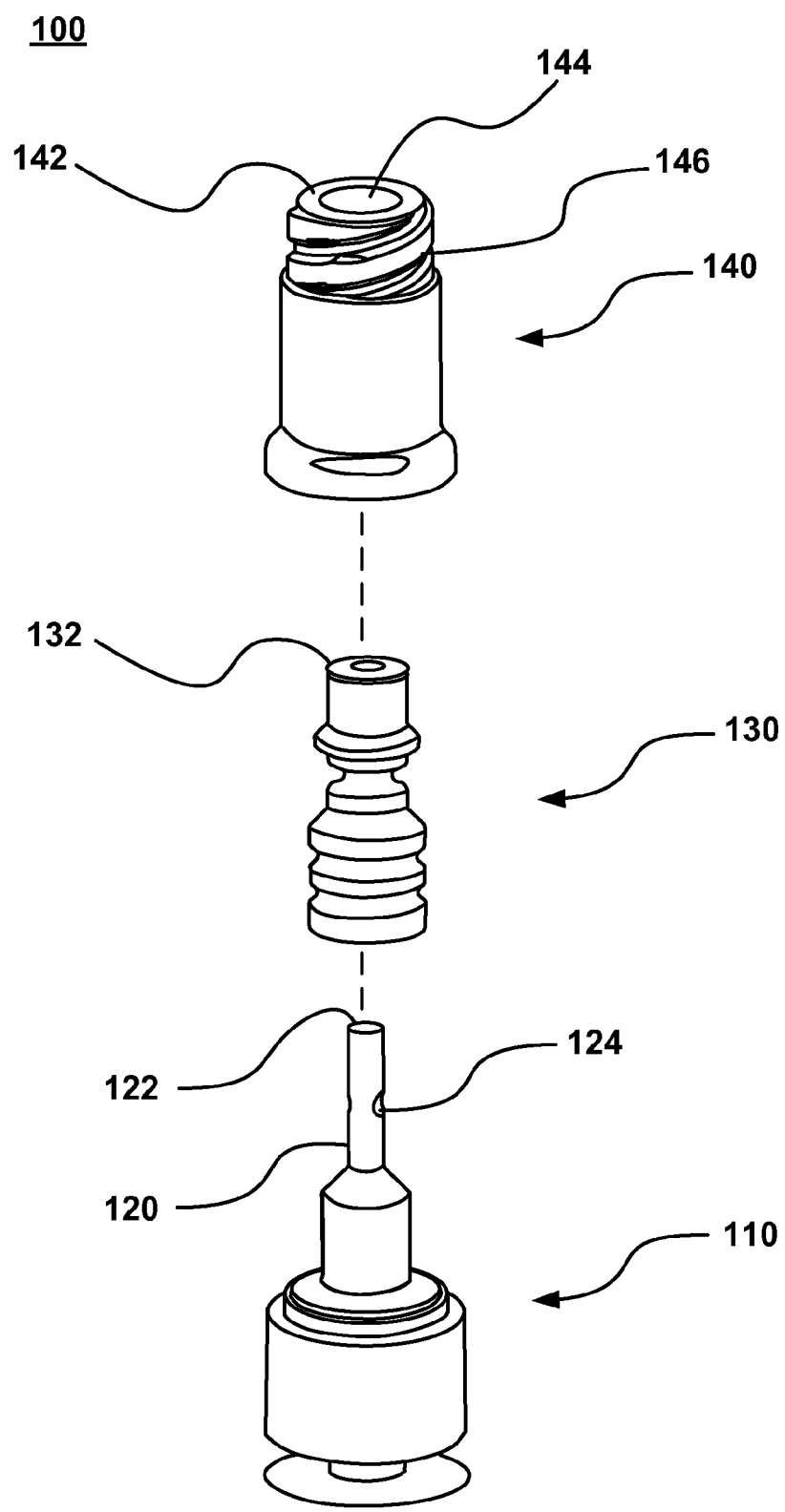
FIGS. 1A-2 depicts embodiments of a needleless valve system.
Figure 1B:
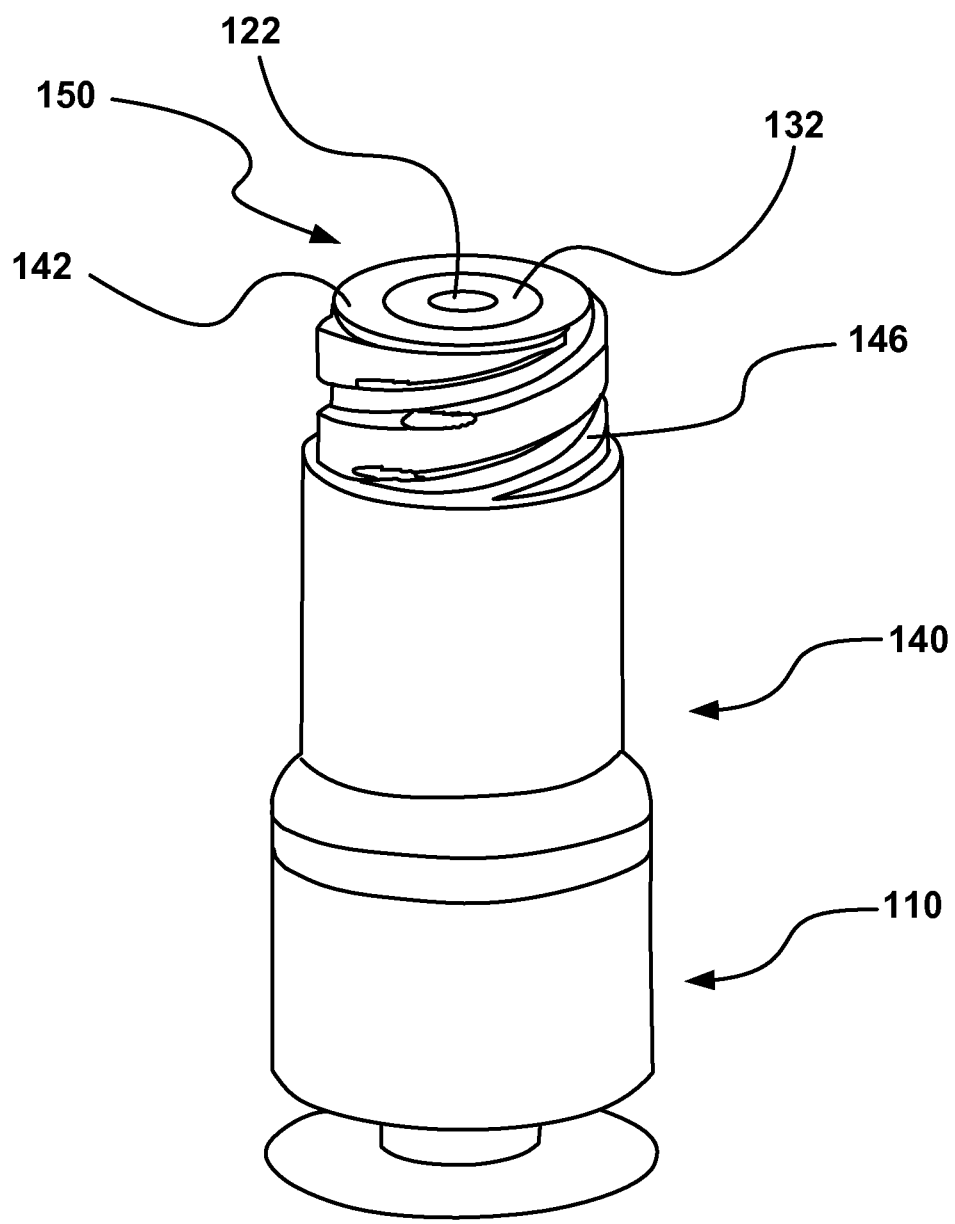
Figure 1C:
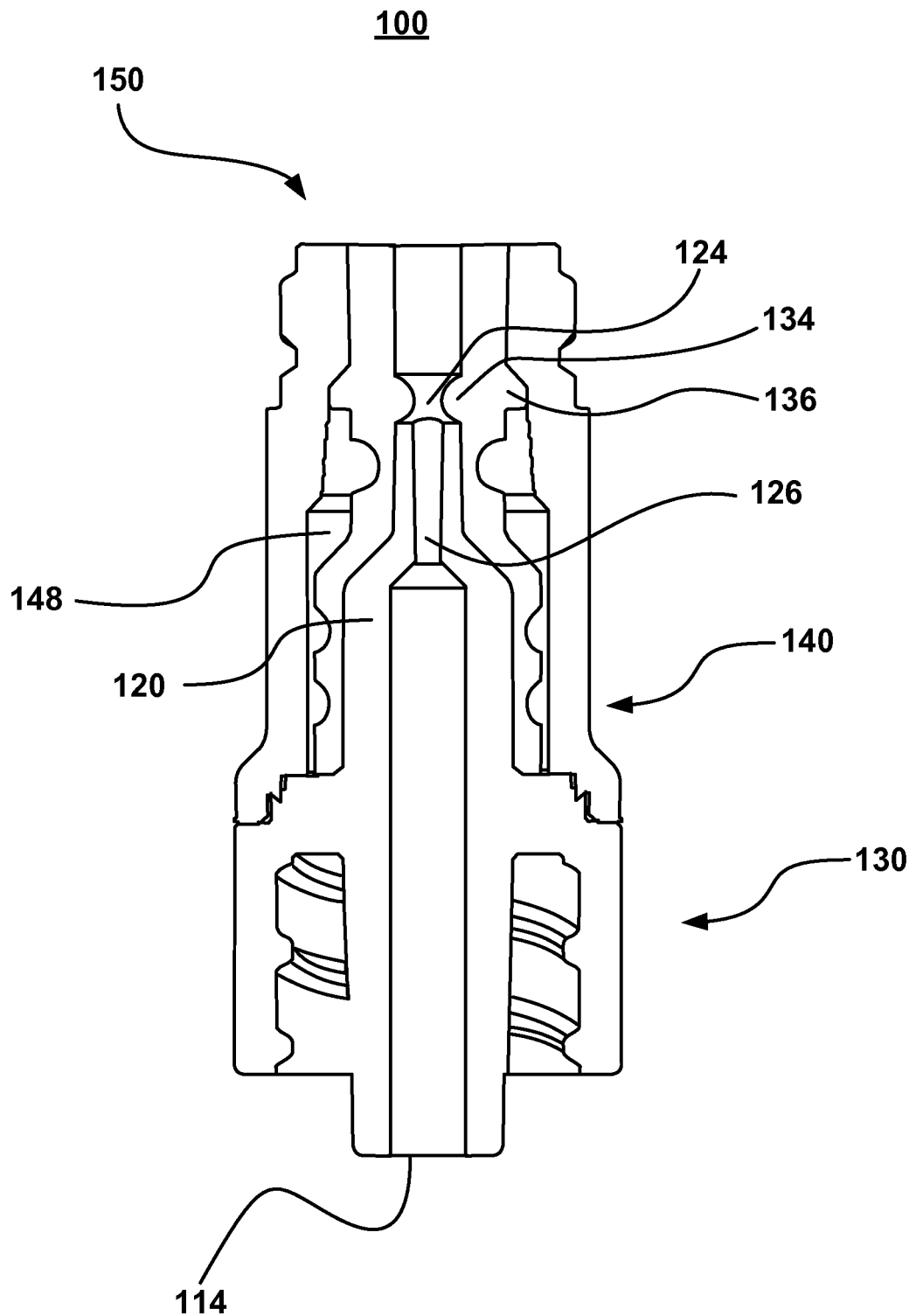
Figure 1D:
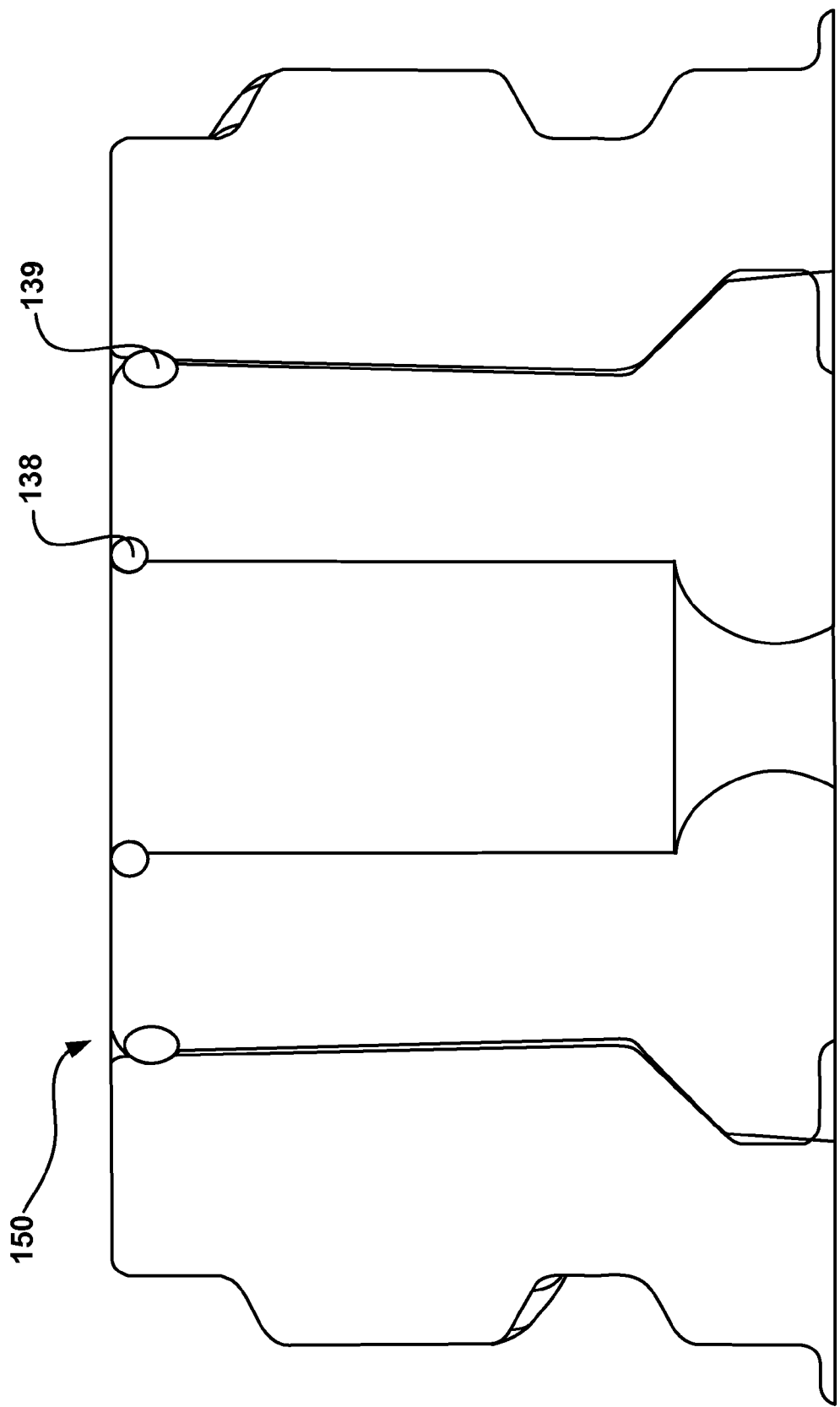

FIGS. 1A-D depicts embodiments of needleless valve system 100 (also referenced herein as system 100) in a sealed or closed position. In particular, FIG. 1A depicts an embodiment of an exploded view of system 100, FIG. 1B depicts an embodiment of a fully assembled system 100, and FIGS. 1C-D depicts embodiments of cross-sectional views of system 100.

System 100 includes base 110 (which includes cannula 120), valve 130 and housing 140. It should be appreciated that base 110 is joined (e.g., ultrasonic welding, adhesive, etc.) with housing 140 such that there is a fluid seal between base 110 and housing 140.

Valve 130 is configured to seal port 124 of cannula 120, which will be described in detail below. Additionally, valve 130 facilitates in sealing port 144 of housing 140. Valve 130 is comprised of a resiliently compressible material that returns to its natural relaxed state when not subject to compression forces.

Cannula 120 is configured to allow for the conveying of fluid in system 100 between port 144 and port 114. In particular, fluid flows through channel 126 when system 100 is in the unsealed or open position.

To seal system 100, valve 130 seals port 124 of cannula 120. Port 124 provides for a fluid channel in the radial direction of cannula 120. In one embodiment, port 124 is a through-hole along a diameter of cannula 120. In another embodiment, port 124 is a hole along a radius of cannula 120.

In one embodiment, valve 130 includes protrusion 134 that seats within port 124. For example, port 124 has two opposing openings and a protrusion seals each of the openings.

In another embodiment, valve 130 includes shoulder 136. Shoulder 136 is disposed opposite protrusion 134. Shoulder 136 seats against an inner surface of housing 140. Shoulder 136 is configured facilitate in the sealing of port 124 by protrusion 134. More specifically, back pressure within fluid channel 126 induces a pressure onto protrusion 134. However, shoulder 136 acts as a buttress and prevents valve 130 (and protrusion 134) from deforming in a radial direction due to the back pressure.

It should be appreciated that port 124 is disposed on a circumference of cannula 120. In contrast, in conventional needleless valve systems, a cannula includes a port on an end portion (e.g., on a longitudinal axis of the cannula).

System 100 includes flat surface 150 when system 100 is in the sealed position. Accordingly, flat surface 150 is able to be properly swabbed. Therefore, pathogens are readily removed and flat surface is properly sanitized.

In particular, tip 122 of cannula 120, tip 132 of valve 130 and tip 142 of housing 140 comprise flat surface 150. As such, system 100 does not require a split septum valve. In contrast, in conventional needleless valve systems, a split-septum valve covers the tip of the cannula and only the split-septum valve and the tip of the housing comprise a top flat surface.

Valve 130 also includes first feature 138 and second feature 139, as depicted in FIG. 1D. First feature 138 and second feature 139 are configured to "squeegee" fluid from the outer surface of cannula 120 and from the inner surface of housing 140, respectively, when valve 130 moves from a compressed position to its relaxed and sealed position, as shown. Accordingly, fluid, such as blood, is expelled from within housing 140.

Figure 2:
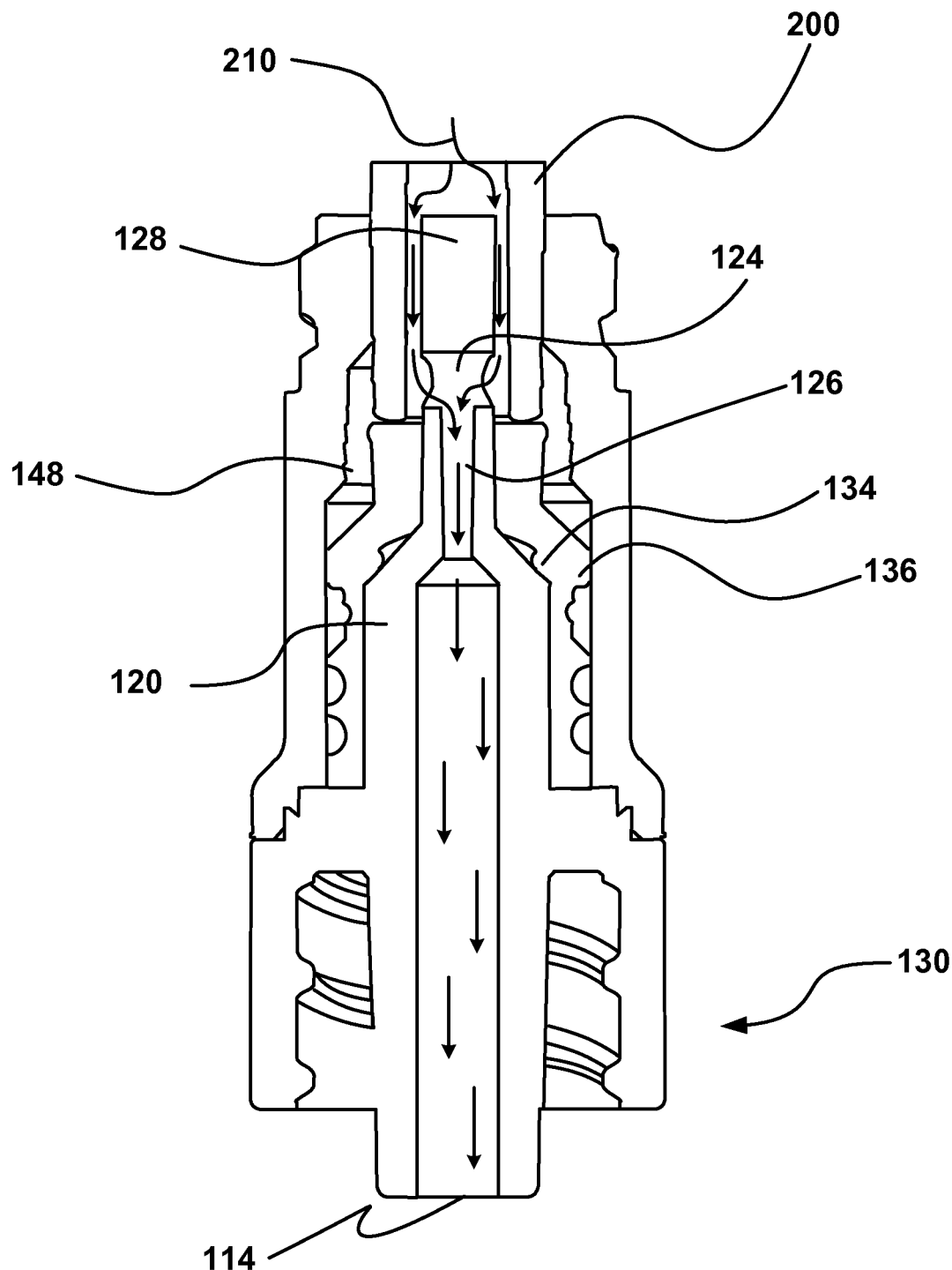

FIG. 2 depicts an embodiment of system 100 in the open or unsealed position. In one embodiment, luer 200 of a needleless device, such as a needleless syringe, enters port 144 and compresses valve 130 within volume 148 of housing 140. In such an embodiment, luer 200 is cooperative with a female luer fitting that threadably engages with male leur fitting 146.

Luer 200 compresses in the longitudinal directions of system 100 and subsequently does not cover port 124. In particular, protrusion 134 resiliently deforms and is forced out of port 124. Accordingly, port 124 is unsealed. Fluid may then travel through system 100 as depicted by fluid flow 210. For example, fluid from an IV bag may flow through system 100 to a patient.

It should be appreciated that fluid flow 210 flows around top portion 128 of cannula 120 and into channel 126 via port 124.

In one embodiment, the fluid can flow in the opposite direction. For example, a clinician may draw blood from a patient and through system 100 into a needleless syringe. For instance, blood flows into system 100 at port 114 and exits system 100 at port 144.

In response to luer 200 being removed from system 100, valve 130 expands to its original position. More specifically, valve 130 expands such that protrusion 134 seats within port 124 and therefore, seals port 124.

As depicted, cannula 120 is coaxial with system 100. As such, fluid flow 210 is through cannula 120. Moreover, the fluid travels exclusively through cannula 120 and does not fill volume 148 or the interior of housing 140. Therefore, there is little residual fluid within system 100.

In contrast, in convention needleless systems, fluid substantially fills the interior volume of the housing which results in a substantial amount of volume. For example, in a convention system, the interior volume may be 1 cubic centimeters (cc). If 10 cc of fluid is intended to be conveyed to a patient via the needleless system, only 9 cc of the fluid reaches the patient, while the other 1 cc remains in the needleless valve as residual fluid.

FIG. 3 depicts an embodiment of method 300 for controlling fluid flow in a needleless valve system. In various embodiments, method 300 is performed at least by needleless valve system 100, as depicted in FIGS. 1A-2.

At 310 of method 300, a port of a cannula is sealed by a valve, wherein the port is disposed along a radius of the cannula. For example, port 124 is sealed by valve 130. Port 124 is disposed at least along a radius of cannula 120.

In one embodiment, at 312, the port is sealed by a protrusion disposed in the port. For example, port 124 is sealed by protrusion 134 that is at least partially disposed in port 124.

At 320, the valve is depressed such that the valve uncovers the port. For example, valve 130 is depressed (in the longitudinal direction or co-axially with housing 140), such that port 124 is uncovered.

In one embodiment, at 322, the valve is depressed by a needleless device. For example, valve 130 is depressed within housing 140 by luer 200.

At 330, fluid is allowed to flow through the port and within the cannula. For example, in response to port 124 being uncovered, fluid flows through port 124 and in channel 126.

At 340, radial deformation of the valve at the port from back pressure in the cannula is prevented. For example, back pressure within cannula 120 can push against protrusion 134. However, shoulder 136, which seats against the inner surface of housing 140, prevents radial deformation of valve 130 at port 124.

At 350, a port of a housing is sealed by the valve. For instance, valve 130 facilitates in sealing port 144 of housing 140.

At 360, a flat surface is provided at a port of a housing, wherein the cannula and the valve are co-planar at the port of the housing. For example, flat surface 150 is provided at port 144. In particular, tip 122 of cannula and tip 132 of valve 130 are co-planar when system 100 is in the sealed position.

At 370, fluid is wiped off of an outer surface of the cannula by the valve. For example, first feature 138 acts as a squeegee and wipes off an outer surface of cannula 120 when valve 130 moves from a compressed state to a relaxed state. Moreover, second feature 139 also acts as a squeegee and wipes off an inner surface of housing 140 when valve 130 moves from a compressed state to a relaxed state. As a result, fluid that is retained between top portion 128 of cannula 120 and an inner surface of housing 140 is expelled out of port 144 when valve 130 moves from a compressed state to a relaxed state.

Various embodiments of the present invention are thus described. While the present invention has been described in particular embodiments, it should be appreciated that the present invention should not be construed as limited by such embodiments, but rather construed according to the following claims.

The invention claimed is:

1. A needleless valve system comprising:
   a cannula comprising a cannula tip, a central lumen, and a radially extending opening in fluid communication with the central lumen;
   a resiliently compressible valve comprising a valve tip, wherein said valve is disposed around said cannula and a protrusion of the valve is received radially within the radially extending opening, and
   a housing comprising a housing tip, wherein said cannula tip, said valve tip, and said housing tip comprise a flat surface when said needleless valve system is in a sealed position;
   wherein when the needleless valve system changes from the sealed position to an open position, the valve deforms and withdraws the protrusion of the valve out of the opening.

2. The needleless valve system of claim 1, wherein said needleless valve system does not require a split septum valve.

3. The needleless valve system of claim 1, wherein said cannula and said valve are co-axially disposed in said housing.

4. The needleless valve system of claim 1, wherein the cannula comprises a radially extending second opening.

5. The needleless valve system of claim 1, wherein said protrusion is radially extending.

6. The needleless valve system of claim 5, wherein said valve further comprises:
   a shoulder disposed opposite said protrusion, wherein said shoulder is configured to resist withdrawal of the protrusion out of the opening by engaging an inner wall of the housing.

7. The needleless valve system of claim 1, wherein said valve is configured to be compressed coaxially within said housing by a male luer.

8. The needleless valve system of claim 1, wherein said valve further comprises:
   ridges disposed along and extending radially inward from an inner surface of said valve that engages the cannula, wherein said ridges are configured for wiping fluid off of an outer surface of said cannula.

9. The needleless valve system of claim 1, further comprising:
   a base joined with said housing, wherein said cannula is formed in said base.

10. A needleless valve system comprising:
    a cannula co-axial with a longitudinal axis of said needleless valve system, said cannula comprising a radially extending port disposed along an outer wall of said cannula; and
    a deformable valve extending around the cannula and having a protrusion extending radially inward configured for sealing said port by extending radially within the port, and a shoulder disposed opposite said protrusion and extending radially outward, the shoulder configured to resist withdrawal of the protrusion out of the opening by engaging an inner wall of a housing.

11. The needleless valve system of claim 10, wherein said needleless valve system does not require a split septum valve.

12. A method for controlling fluid flow in a needleless valve system, said method comprising:
    providing (i) a cannula comprising a central lumen and a radially extending port in fluid communication with the central lumen and (ii) a resiliently compressible valve disposed around said cannula, a protrusion of the valve being received radially within the port while the valve system is in a sealed configuration;

opening the valve system by longitudinally depressing said valve such that said protrusion is withdrawn out of said port, thereby allowing fluid to flow through said port and within said central lumen.

13. The method of claim 12, further comprising sealing said port by longitudinally expanding the valve such that the protrusion is radially received within the port.

14. The method of claim 12, wherein opening said valve system further comprises depressing said valve by a needleless device.

15. The method of claim 12, further comprising:
preventing radial deformation of said valve at said port from back pressure in said cannula.

16. The method of claim 15,
wherein the preventing radial deformation comprises engaging an inner wall of a housing, extending about the valve and cannula, with a shoulder of the valve.

17. The method of claim 12, further comprising:
providing a flat surface at a port of a housing that encompasses the valve and cannula, wherein said cannula and said valve are co-planar at said port of said housing.

18. The method of claim 13, further comprising:
wiping fluid off of an outer surface of said cannula by said valve as the valve is longitudinally expanded.

* * * * *